(12) United States Patent
Niedermeyer

(10) Patent No.: US 12,403,225 B2
(45) Date of Patent: Sep. 2, 2025

(54) FIBER SPINNING PROCESSES FOR APPLYING METAL NANOPARTICLES TO POLYMER DEVICES

(71) Applicant: EVOQ NANO, INC., Salt Lake City, UT (US)

(72) Inventor: William H. Niedermeyer, West Jordan, UT (US)

(73) Assignee: EVOQ NANO, INC., Salt Lake City, UT (US)

( * ) Notice: Subject to any disclaimer, the term of this patent is extended or adjusted under 35 U.S.C. 154(b) by 74 days.

(21) Appl. No.: 18/136,793

(22) Filed: Apr. 19, 2023

(65) Prior Publication Data

US 2023/0338625 A1 Oct. 26, 2023

Related U.S. Application Data

(60) Provisional application No. 63/332,969, filed on Apr. 20, 2022.

(51) Int. Cl.
| | | |
|---|---|---|
| *D01D 7/00* | (2006.01) | |
| *A61L 31/02* | (2006.01) | |
| *A61L 31/12* | (2006.01) | |
| *A61L 31/16* | (2006.01) | |
| *C08J 3/205* | (2006.01) | |
| *C08K 3/08* | (2006.01) | |

(Continued)

(52) U.S. Cl.
CPC ........... *A61L 31/128* (2013.01); *A61L 31/022* (2013.01); *A61L 31/16* (2013.01); *C08J 3/2053* (2013.01); *C08K 3/08* (2013.01); *C08K 7/18* (2013.01); *D01D 5/0038* (2013.01); *D01D 5/0046* (2013.01); *D01F 1/103* (2013.01); *A61L 2400/12* (2013.01); *C08J 2323/06* (2013.01); *C08K 2003/0806* (2013.01); *C08K 2003/0831* (2013.01); *C08K 2201/011* (2013.01)

(58) Field of Classification Search
CPC .. C08J 3/2053; C08K 3/08; C08K 2003/0806; C08K 2003/0831; C08K 2201/011; D01D 5/0038; D01D 5/0046; D01D 5/06; D01D 7/00; D01F 1/10; D01F 1/103
USPC .... 264/184, 211, 211.12, 465; 524/779, 780
See application file for complete search history.

(56) References Cited

U.S. PATENT DOCUMENTS

| | | |
|---|---|---|
| 3,867,332 A | 2/1975 | Chimura et al. |
| 6,340,443 B1 | 1/2002 | Kurihara et al. |

(Continued)

FOREIGN PATENT DOCUMENTS

KR 10-1000266 B1 12/2010

OTHER PUBLICATIONS

International Search Report and Written Opinion received for PCT Patent Application No. PCT/US2022/047414, mailed on Jan. 19, 2023, 10 pages.

(Continued)

*Primary Examiner* — Leo B Tentoni
(74) *Attorney, Agent, or Firm* — Workman Nydegger

(57) ABSTRACT

Disclosed are polymer fibers incorporating metal nanoparticles and medical devices made therefrom. The disclosed polymer fibers can be utilized to form medical devices, including implantable medical devices, with effective antimicrobial properties. The disclosed polymer fibers incorporate metal nanoparticles that function without the release of metal (e.g., silver) ions.

20 Claims, 9 Drawing Sheets

(51) Int. Cl.
    *C08K 7/18*    (2006.01)
    *D01D 5/00*    (2006.01)
    *D01F 1/10*    (2006.01)

(56) References Cited

U.S. PATENT DOCUMENTS

| | | |
|---|---|---|
| 7,880,175 B2 | 2/2011 | Shin et al. |
| 2006/0202382 A1 | 9/2006 | Lin |
| 2010/0050872 A1* | 3/2010 | Lee ................ B01D 46/546 |
| | | 264/465 X |
| 2011/0201242 A1* | 8/2011 | Hur ..................... D01F 1/10 |
| | | 436/163 |
| 2012/0114722 A1* | 5/2012 | Ballard ............... D01F 1/103 |
| | | 264/465 X |
| 2013/0280471 A1 | 10/2013 | Johansson et al. |
| 2016/0082514 A1* | 3/2016 | Niedermeyer ......... B23K 26/06 |
| | | 75/347 |
| 2019/0091071 A1 | 3/2019 | VanDelden |

OTHER PUBLICATIONS

International Search Report and Written Opinion received for PCT Patent Application No. PCT/US23/019272, mailed on Jul. 24, 2023, 12 pages.

Zhang et al., "A Review on Preparation and Applications of Silver-Containing Nanofibers", Nanoscale Res Lett., 2016, vol. 11, 80, pp. 1-8.

\* cited by examiner

FIBER SPINNING PROCESSES FOR APPLYING METAL NANOPARTICLES TO POLYMER DEVICES

CROSS-REFERENCE TO RELATED APPLICATIONS

This application claims priority to and the benefit of U.S. Provisional Application No. 63/332,969, filed Apr. 20, 2022, the entirety of which is incorporated herein by reference.

BACKGROUND

Technical Field

This disclosure relates to polymer compositions containing antimicrobial nanoparticles, devices formed therefrom, and fiber spinning manufacturing processes for forming such polymer compositions and devices.

Related Technology

Polymers used in medical and other applications are typically inexpensive and can be used for many different functions. Polymeric articles of manufacture may be manufactured using injection molding processes. One issue with mold injected polymers is that the surface finish of the product can be sponge-like, with pores that can extend several microns deep into the product. FIG. 1, for example, is a scanning transmission electron microscope (STEM) image of a surface of polystyrene from a thermal extruded pellet. The polymer surface has a high degree of porosity that can harbor bacteria and other microbes. Such microbial growth can be concerning for hospitals and others in the medical field. The management of polymers used in areas of high sensitivity, including many medical applications, requires expensive and rigorous sterilization and storage procedures. Even so, aggravated tissues and infections are known to result from the use of compromised polymers used to deliver substances to patients and/or implanted into patients. Drug resistant microbial infections may also result from the use of compromised polymer products, causing expensive healthcare maintenance and even death.

The overuse of antibiotics has contributed, in some cases, to antibiotic resistant bacteria and other treatment resistant microbes. There is concern that an increase in antibiotic resistance may lead to microbes that are untreatable with conventional technologies. Currently, there are few methods of disinfection and microbial control that don't require the use of conventional antibiotics. In some cases, medical devices that incorporate antibiotics cannot stop formation of biofilms and/or cannot prevent infection from bacteria with antibiotic resistance. In such cases, the use of antibiotics in polymeric materials does not protect the patient from infection and may even give a false sense of security.

There are attempts to incorporate ionic colloidal silver and silver nanoparticles into polymeric materials to import antimicrobial activity to polymers. However, antimicrobial resistance has now been discovered for colloidal silver (i.e., silver nanoparticles manufactured by conventional chemical reduction processes, typically with some form of capping agent) and ionic silver. McNeilly et al., "Emerging Concern for Silver Nanoparticle Resistance in *Acinetobacter baumannii* and Other Bacteria," *Front. Microbiol.*, 16 Apr. 2021, discuss the emergence of several antibiotic-resistant bacteria, including *Acinetobacter baumannii, Enterococcus faecium, Staphylococcus aureus, Klebsiella pneumoniae, Acinetobacter baumannii, Pseudomonas aeruginosa,* and *Enterobacter* spp. Of these, *A. baumannii* was of particular concern and was found to also have developed resistance to colloidal silver nanoparticles, as were *E. Coli, Enterobacter cloacae, S. typhimurium, B. subtilis, S. aureus. P. aeruginosa, K pneumoniae, Serratia marcescens, Acinetobacter* spp.

Silver, "Bacterial silver resistance: molecular biology and uses and misuses of silver compounds," *FEMS Microbiology Reviews*, Volume 27, Issue 2-3, June 2003, Pages 341-35, discusses silver-resistant *Salmonella,* and *Escherichia coli*. Elkrewi, et al., "Cryptic silver resistance is prevalent and readily activated in certain Gram-negative pathogens," *J. Antimicrob. Chemother.*, 2017 Nov. 1; 72(11): 3043-3046 discloses colloidal silver nanoparticle resistance by gram negative pathogens, such as *Enterobacter* spp., *Klebsiella* spp. *Escherichia coli, Pseudomonas aeruginosa, Acinetobacter* spp., *Citrobacter* spp., and *Proteus* spp. Hosney, "The increasing threat of silver-resistance in clinical isolates from wounds and burns," *Infect Drug Resist.* 2019; 12: 1985-2001 discusses colloidal silver-resistant *Klebsiella pneumoniae, Staphylococcus aureus, Escherichia coli, Enterobacter cloacae, Pseudomonas aeruginosa,* and *Acinetobacter baumannii*. Percival, et al., "Bacterial resistance to silver in wound care, *J. Hospital Infection*, Vol. 60, Issue 1, May 2005, pp. 1-7, discusses the fear and possibility of colloidal silver-resistant microbes in wounds. Kędziora, et al., "Consequences Of Long-Term Bacteria's Exposure To Silver Nanoformulations With Different PhysicoChemical Properties," *Intl. J. of Nanomedicine,* 2020:15 199-213, discusses colloidal silver-resistant gram positive and gram negative bacteria.

An article entitled "Are Silver Nanoparticles a Silver Bullet Against Microbes?" Jul. 13, 2021, https://news.engineering.pitt.edu/are-silver-nanoparticles-a-silver-bullet-against-microbes/(accessed Oct. 12, 2022), discusses colloidal silver nanoparticle resistant *E. coli.*, stating: "In the beginning, bacteria could only survive at low concentrations of silver nanoparticles, but as the experiment continued, we found that they could survive at higher doses . . . . Interestingly, we found that bacteria developed resistance to the silver nanoparticles but not their released silver ions alone." The group sequenced the genome of the *E. coli* that had been exposed to silver nanoparticles and found a mutation in a gene that corresponds to an efflux pump that pushes heavy metal ions out of the cell. "It is possible that some form of silver is getting into the cell, and when it arrives, the cell mutates to quickly pump it out . . . . More work is needed to determine if researchers can perhaps overcome this mechanism of resistance through particle design."

Silver nanoparticles made by conventional chemical synthesis methods have external bond angles and edges where silver ions can be released, even though the bulk nanoparticles are ground state. Adding metal nanoparticles that release ions into polymers yields nanoparticle-impregnated polymers and plastics that are a source of unwanted metal ions, such as silver ions, which may be toxic to human and animal tissues under excess exposure. Moreover, the release of ions may decrease over time. So even where there are beneficial antimicrobial effects associated with silver ion release, such effects will degrade over time as ions are leached out of the bulk polymer material. Where silver ion release is the major mode of antimicrobial action, which is the case for conventional colloidal silver products, the antimicrobial activity of the polymer will likewise degrade over time.

Additionally, exposure to solar radiation can cause weakening and other structural damage to polymers. When absorbed by polymers, UV energy may excite electrons, creating free radicals that can lead to degradation of the plastic. Polymers that have been affected by UV radiation may appear chalky, the surface of the polymer may become brittle, and there may be a noticeable color change on the surface of the polymer. UV-caused degradation may lead to cracks in the polymer product and may cause the product to fail altogether. For example, UV radiation hitting polypropylene and/or low-density polyethylene may interact with tertiary carbon bonds within their structures, which can then interact with atmospheric oxygen. This can produce carbonyl groups in the main chain of the structure, leaving the plastic product prone to cracking or discoloration.

Ultraviolet radiation B ("UVB radiation") is generally considered to lie within the range of about 280 to about 315 nanometers in wavelength. Ultraviolet radiation A ("UVA radiation") is generally considered to lie within the range of about 315 to about 400 nanometers in wavelength. Ultraviolet radiation C (UVC) is generally considered to lie within the range of about 100 to about 280 nanometers in wavelength.

In view of the foregoing, there remains a need to find improved polymer materials that exhibit effective antimicrobial properties and that are effective for use in medical devices, including implantable medical devices.

SUMMARY

Disclosed are polymer compositions incorporating metal nanoparticles, medical devices made therefrom, and fiber spinning methods for forming such polymer compositions and devices. The disclosed polymer compositions can be utilized to form medical devices, including implantable medical devices, with effective antimicrobial properties. The disclosed polymer compositions incorporate metal nanoparticles that function without the release of metal (e.g., silver) ions. The disclosed polymer materials can also effectively resist UV damage when exposed to sunlight and/or other sources of UV light.

In some embodiments, the disclosed polymer compositions include wavelength-shifting metal nanoparticles that function to protect exposed surfaces from UV radiation. For example, the polymer compositions can down-convert incoming UV light to light of longer wavelength that is less damaging, or non-damaging, to polymer linkages.

The disclosed polymer compositions comprising metal nanoparticles also have antimicrobial properties to prevent colonization of microbes thereon, including preventing colonization of microbes within pores of the polymer materials and structures formed therefrom. Such nanoparticle-modified polymers are less prone to developing silver nanoparticle antibiotic resistance, as often occurs with conventional colloidal silver made via chemical synthesis. Surprisingly and unexpectedly, it has been found that nonionic silver nanoparticles formed by laser ablation do not lead to silver nanoparticle resistance, at least not to the same degree as occurs when using conventional colloidal silver or silver nanoparticles made by chemical synthesis, which are known to release silver ions as their primary mode of antimicrobial activity.

Metal (e.g., silver) nanoparticles produced by laser ablation methods (and possessing smooth spherical morphologies and narrow size distributions) can be integrated into polymers to mitigate colonization of bacteria or other microbes. Unexpectedly, spherical-shaped silver nanoparticles made by laser ablation and having a narrow particle size distribution do not result in microbial resistance to the same degree as conventional colloidal silver or silver nanoparticles formed via chemical synthesis.

In some embodiments, spherical metal (e.g., silver) nanoparticles have a mean diameter and a particle size distribution in which at least 99% of the spherical metal nanoparticles have a particle size within 30% of the mean diameter, or within 20% of the mean diameter, or within 10% of the mean diameter and/or wherein at least 99% of the spherical metal nanoparticles have a diameter within ±3 nm of the mean diameter, or within ±2 nm of the mean diameter, or within ±1 nm of the mean diameter.

In some embodiments, the compositions may comprise coral-shaped metal nanoparticles alternative to or in addition to the spherical metal nanoparticles. Coral-shaped metal (e.g., gold) nanoparticles have a non-uniform cross section and a globular structure formed by multiple, non-linear strands joined together without right angles.

In some embodiments, metal nanoparticles can comprise spherical-shaped metal (e.g., silver) nanoparticles and/or coral-shaped metal (e.g., gold) nanoparticles. In some embodiments the coral-shaped metal nanoparticles can be used together with spherical-shaped metal nanoparticles. The coral-shaped nanoparticles can beneficially potentiate the spherical-shaped metal nanoparticles.

In some embodiments, metal nanoparticles can comprise at least one metal selected from the group consisting of silver, gold, platinum, palladium, rhodium, osmium, ruthenium, rhenium, molybdenum, copper, iron, nickel, tin, beryllium, cobalt, antimony, chromium, manganese, zirconium, tin, zinc, tungsten, titanium, vanadium, lanthanum, cerium, heterogeneous mixtures thereof, and alloys thereof. Nanoparticles comprised of silver, gold, and mixtures and alloys thereof can be particularly effective.

In some embodiments, the polymer compositions can be made from liquid polymer compositions in which metal nanoparticles are incorporated therein, such as by mixing the metal nanoparticles in an uncured polymer solution or polymer melt, and drawing polymer fibers therefrom using an electrospinning or wet spinning process. The metal nanoparticles become mixed throughout the formed polymer fibers.

The portion of metal nanoparticles on the surface of the polymer material and/or embedded within pores will provide antimicrobial activity to prevent microbial growth on the polymer material. The metal nanoparticles will also protect the polymers materials from damage by UV radiation by down-converting incoming UV energy to a lower energy wavelength(s) that is less damaging, or non-damaging, to the polymer material.

The polymer compositions disclosed herein can beneficially provide antimicrobial and UV protective effects for extended durations, without depletion of the nanoparticles, even after abrasion or machining. For example, because the embedded nanoparticles do not rely on ion release as the primary means of antimicrobial activity, the polymer compositions disclosed herein can provide this function for longer than similar polymer compositions utilizing conventional nanoparticles formed via chemical synthesis.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification. In the Drawings, like reference numerals may be utilized to designate corresponding or similar parts in the various Figures, and the various elements depicted are not necessarily drawn to scale, wherein:

DETAILED DESCRIPTION

I. Introduction

Figure 1:
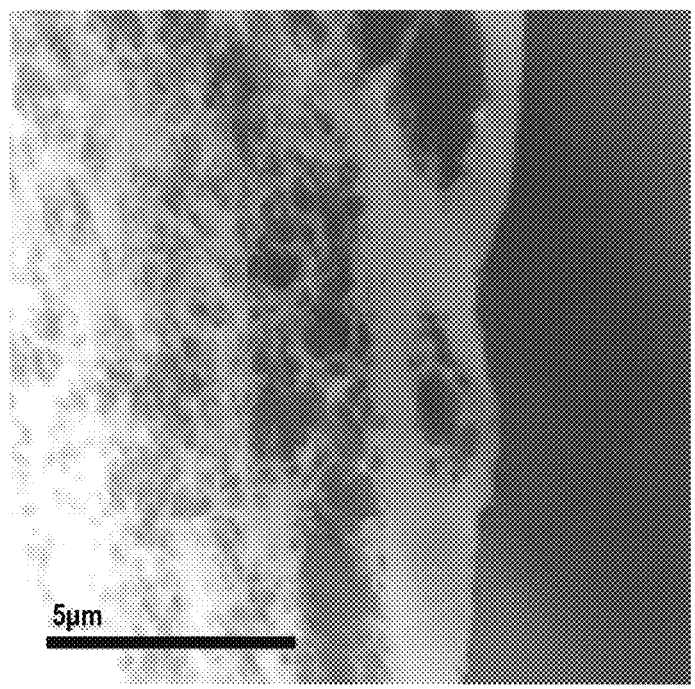
FIG. 1 is a scanning transmission electron microscope image of a surface of polystyrene from thermal extruded pellets.

The term "nanoparticle" often refers to particles having a largest dimension of less than 100 nm. Bulk materials typically have constant physical properties regardless of size, but at the nanoscale, size dependent properties are often observed. Thus, properties of materials change as their size approaches the nanoscale and as the percentage of atoms at the surface of a material becomes significant. For bulk materials larger than one micrometer (or micron), the percentage of atoms at the surface is insignificant in relation to the number of atoms in the bulk of the material. The interesting and sometimes unexpected properties of nanoparticles are therefore largely due to the large surface area of the material, which dominates the contributions made by the relatively small bulk of the material.

Polymer compositions disclosed herein can be made from liquid polymer compositions in which metal nanoparticles are incorporated, such as by mixing the metal nanoparticles in an uncured polymer solution or polymer melt, and drawing polymer fibers therefrom using an electrospinning or wet spinning process. The metal nanoparticles become mixed throughout the formed polymer fibers.

As used herein, a "polymer composition" refers to the polymer fiber product resulting from the disclosed electrospinning or wet spinning processes and may be used synonymously with terms such as "polymer fiber" and like terms. A "polymer solution" or "polymer melt" refers to the liquid and/or uncured composition prior to being drawn into a fiber through one of the foregoing processes. A "polymer solution" may be an uncured solution comprising monomers and/or oligomers that undergo polymerization and/or cross-linking upon being drawn into fibers, whereas a "polymer melt" may be a polymer that is heated to melting and resolidifies upon being drawn into fibers.

Where some examples may refer to a polymer solution and others may refer to a polymer melt, it will be understood that the same principles apply to either embodiment. As disclosed herein, metal nanoparticles may be mixed with the polymer solution or polymer melt prior to the fiber spinning process such that the resulting polymer composition incorporates the metal nanoparticles.

Examples of polymer compositions that may be utilized in the disclosed embodiments include silicone, epoxies, polystyrene (PS), polyethylene (PE) (including low density, linear low density, and high density PE), ethylene-vinyl acetate copolymer (EVA), polycarbonate (PC), polyurethane (PU), polyether ether ketone (PEEK), polylactic acid (PLA), polyhydroxyalkanoate (PHA), polyester (PES), polypropylene (PP), polyethylene terephthalate (PET), polymethyl methacrylate (PMMA), polybutylene terephthalate (PBT), phenol-formaldehyde (PF), nylon/polyimide (PA), melamine formaldehyde (MF), polytetrafluoroethylene (PTFE), polyvinyl chloride (PVC), polyvinyl pyrrolidone (PVP), acrylonitrile butadiene styrene terpolymers (ABS), styrene block copolymers (SBC), rubber latex (natural or synthetic), nitriles such as nitrile-butadiene rubber (NBR), aramid fibers such as Kevlar, carbon fiber reinforced polymers, and combinations thereof.

II. Nanoparticles

The metal nanoparticles used in the disclosed polymer compositions can be nonionic, ground state, and without external edges or bond angles that cause release of metal ions. Spherical-shaped metal nanoparticles are typically used to kill microbes, although coral-shaped metal nanoparticles can provide anti-microbial activity, typically in combination with spherical metal nanoparticles.

In some embodiments, the metal nanoparticles may comprise or consist essentially of nonionic, ground state metal nanoparticles without external edges or bond angles that cause release of metal ions. Examples include spherical metal nanoparticles, coral-shaped metal nanoparticles, and blends of spherical-shaped and coral-shaped metal nanoparticles.

Conventional silver nanoparticles manufactured via chemical reduction (typically involving a capping agent) tend to exhibit a clustered, crystalline, faceted, or hedron-like shape rather than a true spherical shape with round and smooth surfaces. Such nanoparticles often cluster and can have a relatively broad size distribution. In some cases, conventional silver nanoparticles are formed as shells of silver formed over a non-metallic seed material.

In contrast, the spherical-shaped nanoparticles that can be included in the polymer compositions disclosed herein can exhibit one or more of: (1) solid metal form, (2) substantially unclustered, (3) exposed/uncoated surfaces, (4) smooth surface morphology, and/or (4) narrow size distribution. As used herein, an "exposed" or "uncoated" surface is one that omits capping agents and instead directly exposes the metal surface to the environment.

The metal nanoparticles of the disclosed polymer compositions, including spherical-shaped and coral-shaped nanoparticles, may comprise any desired metal, mixture of metals, or metal alloy, including at least one of silver, gold, platinum, palladium, rhodium, osmium, ruthenium, rhenium, molybdenum, copper, iron, nickel, tin, beryllium, cobalt, antimony, chromium, manganese, zirconium, tin, zinc, tungsten, titanium, vanadium, lanthanum, cerium, heterogeneous mixtures thereof, or alloys thereof. Nanoparticles comprised of silver, gold, and mixtures and alloys thereof can be particularly effective.

In some embodiments, gold (Au) nanoparticles are included in the polymer compositions and function to downshift incoming UV radiation. The gold nanoparticles may down-convert the light waves into less energetic and harmful light of longer wavelength(s). The gold nanoparticles may down-convert the light wavelengths towards the red zone of the light spectrum. In some embodiments, the gold nanoparticles are spherical-shaped. In some embodiments, the gold nanoparticles are approximately 1 to 40 nm in diameter.

Nanoparticle compositions may include spherical metal nanoparticles, coral-shaped metal nanoparticles, or a combination of the two. Spherical metal nanoparticles typically have greater antimicrobial activity, although coral-shaped metal nanoparticles can also provide anti-microbial activity and can potentiate the antimicrobial activity of spherical-shaped metal nanoparticles when the two are combined.

Nonionic, ground state, spherical-shaped metal nanoparticles with no external edges or bond angles, and compositions containing such nanoparticles, can be made according to the disclosure of U.S. Pat. Nos. 9,849,512, 10,137,503, and 10,610,934. Nonionic, ground state, coral-shaped metal nanoparticles with no external edges or bond angles, and compositions containing such nanoparticles, can be made according to the disclosure of U.S. Pat. No. 9,919,363. Compositions that contain a mixture of spherical metal nanoparticles and coral-shaped metal nanoparticles are disclosed in U.S. Pat. No. 9,434,006. Each of the foregoing patents are incorporated herein by reference in its entirety.

Liquid mediums in which the nanoparticles are mixed (e.g., the polymer solution or polymer melt) may include nanoparticles at a concentration of about 50 ppb to about 100 ppm, or about 100 ppb to about 50 ppm, or about 200 ppb to about 20 ppm, or about 400 ppb to about 10 ppm, or about 600 ppb to about 6 ppm, or about 800 ppb to about 4 ppm, or about 1 ppm to 3 ppm, or about 2 ppm, or a range using any combination of the foregoing values as endpoints, by weight of the liquid medium applied to the polymer composition.

After the nanoparticles are incorporated into the polymer composition (e.g., incorporated in the formed fibers), the nanoparticles may be included at about 0.5 mg/kg to about 8 mg/kg, such as about 1 mg/kg, 2 mg/kg, 3 mg/kg, 4 mg/kg, 5 mg/kg, 6 mg/kg, 7 mg/kg, or a range with any combination of the foregoing values as endpoints.

The spherical-shaped metal nanoparticles can have an average particle size (i.e., diameter) in a range of about 1 nm to about 20 nm, such as about 3 nm to about 14 nm, or about 4 nm to about 13 nm, or about 5 nm to about 12 nm, or about 6 nm to about 10 nm. In some embodiments, spherical metal nanoparticles can have a diameter of about 40 nm or less, about 35 nm or less, about 30 nm or less, about 25 nm or less, about 20 nm or less, about 15 nm or less, about 10 nm or less, about 7.5 nm or less, or about 5 nm or less. The compositions may include nanoparticles in a concentration range with endpoints defined by any two of the foregoing values.

As used herein, unless indicated otherwise, the mean diameter (i.e., average particle size) refers to the number average, which can be determined according to standard methods known in the art. As an example, the mean diameter may be determined via microscopy (e.g., scanning transmission electron microscope (STEM)) and analysis of resulting images. Another suitable method for determining mean diameter of a set of metal nanoparticles is dynamic light scattering (DLS), which is typically reported on a volume basis.

The spherical metal nanoparticles can have a particle size distribution wherein at least 99% of the metal nanoparticles have a particle size within 30% of the mean diameter, or within 20% of the mean diameter, or within 10% of the mean diameter and/or wherein at least 99% of the spherical-shaped nanoparticles have a diameter within ±3 nm of the mean diameter, or within ±2 nm of the mean diameter, or within ±1 nm of the mean diameter. The spherical nanoparticles can have a potential of at least about ±10 mV (absolute value), or at least about ±15 mV, or at least about ±20 mV, or at least about ±25 mV, or at least about ±30 mV.

In some embodiments, coral-shaped metal nanoparticles can be used in conjunction with spherical metal nanoparticles. In general, spherical metal nanoparticles can be smaller than coral-shaped metal nanoparticles and in this way can provide very high surface area for catalyzing desired reactions or providing other desired benefits. On the other hand, the generally larger coral-shaped nanoparticles can exhibit higher surface area per unit mass compared to spherical nanoparticles because coral-shaped nanoparticles have internal spaces and surfaces rather than a solid core and only an external surface.

In at least some cases, providing nanoparticle compositions containing both spherical-shaped and coral-shaped nanoparticles can provide synergistic results. Coral-shaped nanoparticles can help carry and/or potentiate the activity of spherical-shaped nanoparticles in addition to providing their own unique benefits. For example, smaller particles may offer better relative protection against UVB radiation, while relatively larger particles may offer better protection against UVA radiation. In some embodiments, a combination of spherical-shaped and coral-shaped nanoparticles can lead to synergistic, broad-spectrum protection with a greater amount of protection (e.g., amount of UV radiation reflected) per amount of active ingredient relative to single sized and/or shaped compositions.

In some embodiments, the mass ratio of spherical nanoparticles to coral-shaped nanoparticles in the nanoparticle composition can be in a range of about 1:1 to about 50:1, or about 2.5:1 to about 25:1, or about 5:1 to about 20:1, or about 7.5:1 to about 15:1, or about 9:1 to about 11:1, or about 10:1. The particle number ratio of spherical nanoparticles to coral-shaped nanoparticles in the nanoparticle composition can be in a range of about 10:1 to about 500:1, or about 25:1 to about 250:1, or about 50:1 to about 200:1, or about 75:1 to about 150:1, or about 90:1 to about 110:1, or about 100:1.

In some embodiments, at least a portion of the metal nanoparticles are selected to selectively reflect, block, and/or scatter a particular range of solar radiation. For example, a first set of metal nanoparticles may be selected as spherical-shaped metal nanoparticles having a smaller relative size and which therefore selectively reflect, scatter, and/or block more particularly UVB radiation, while a second set of metal nanoparticles may be selected as coral-shaped metal nanoparticles having a larger relative size and which therefore selectively reflect, scatter, and/or block more particularly UVA radiation.

In some embodiments, the polymer compositions include at least one spherical anti-microbial nanoparticle component and larger coral-shaped nanoparticle component.

III. Antimicrobial Function of Nanoparticles

Figure 2A:
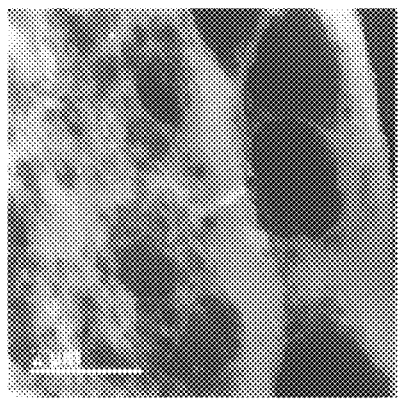
FIGS. 2A-2C illustrate thermoplastics containing Ag nanoparticles.
Figure 2B:
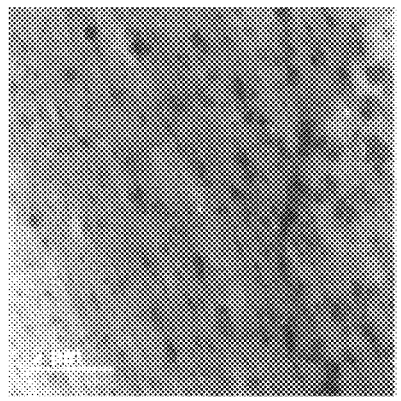
Figure 2C:
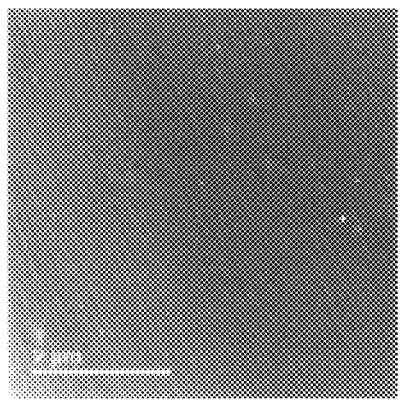

FIGS. 2A-2C are STEM images that illustrate thermoplastics containing silver (Ag) nanoparticles, which provides the polymer composition with antimicrobial and/or wavelength shifting properties.

Figure 3A:
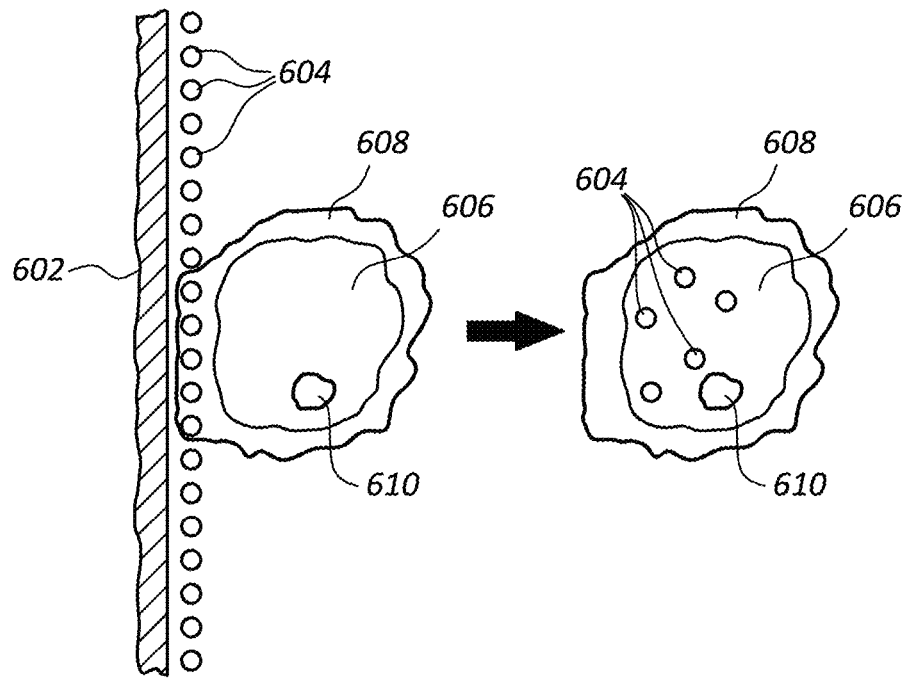
FIGS. 3A-B schematically illustrate a microbe after having absorbed spherical-shaped metal nanoparticle from a substrate and disulfide bonds being catalytically denatured by a spherical-shaped nanoparticle.
Figure 3B:
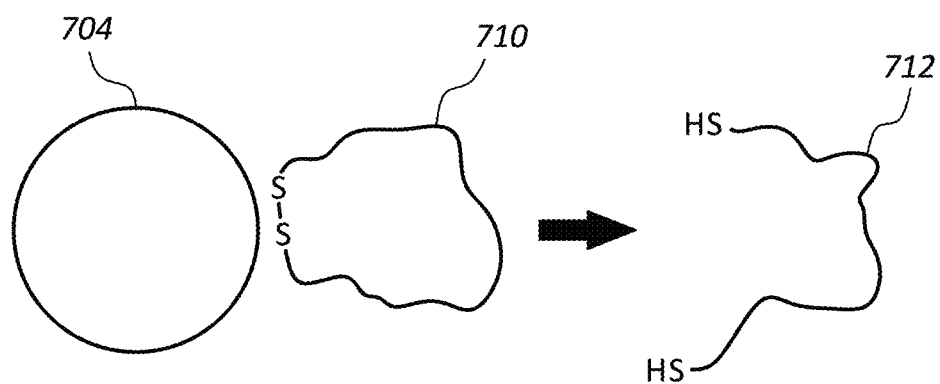

FIGS. 3A-3B schematically illustrate a microbe after having absorbed spherical-shaped metal nanoparticle from a substrate and disulfide bonds being catalytically denatured by a spherical-shaped nanoparticle. FIG. 3A schematically illustrates a microbe 608 having absorbed spherical-shaped nanoparticles 604 from a solid substrate 602, such as by active absorption or other transport mechanism. Alternatively, spherical-shaped nanoparticles 604 can be provided in a composition (not shown), such as in a liquid or gel carrier. The nanoparticles 604 can freely move throughout the interior 606 of microbe 608 and come into contact with one or more vital proteins or enzymes 610 that, if denatured, will kill or disable the microbe.

One way that nanoparticles may kill or denature a microbe is by catalyzing the cleavage of disulfide (S—S) bonds within a vital protein or enzyme. FIG. 3B schematically illustrates a microbe protein or enzyme 710 with disulfide bonds being catalytically denatured by an adjacent spherical-shaped nanoparticle 704 to yield denatured protein or enzyme 712. In the case of bacteria or fungi, the cleavage of disulfide bonds and/or cleavage of other chemical bonds of vital proteins or enzymes may occur within the cell interior and thereby killing the microbe in this manner. Such catalytic cleavage of disulfide (S—S) bonds is facilitated by the generally simple protein structures of microbes, in which many vital disulfide bonds are exposed and readily cleaved by catalysis.

Another potential mechanism by which metal (e.g., silver) nanoparticles can kill microbes is through the production of active oxygen species, such as peroxides, which can oxidatively cleave protein bonds, including but not limited to amide bonds.

Notwithstanding the lethal nature of nonionic metal nanoparticles relative to microbes, they have been shown to be harmless and non-toxic to humans, mammals, and animals, which contain much more complex protein structures compared to simple microbes in which most or all vital disulfide bonds are shielded by other, more stable regions of the protein. In many cases the nonionic nanoparticles do not interact with or attach to human cells, other mammalian cells, or other animal cells, and can be quickly and safely expelled through the urine without damaging kidneys or other cells, tissues, or organs.

In the case of spherical silver (Ag) nanoparticles, the interaction of the silver (Ag) nanoparticle(s) within a microbe has been demonstrated to be particularly lethal without the need to rely on the production of silver ions ($Ag^+$) to provide the desired antimicrobial effects, as is typically the case with conventional colloidal silver compositions. The ability of silver (Ag) nanoparticles to provide effective microbial control without any significant or actual release of toxic silver ions ($Ag^+$) into the patient or the surrounding environment is a substantial advancement in the art. Whatever amount or concentration of silver ions released by silver nanoparticles, if any, is well below known or inherent toxicity levels for animals, such as mammals, birds, reptiles, fish, and amphibians.

Figure 4:
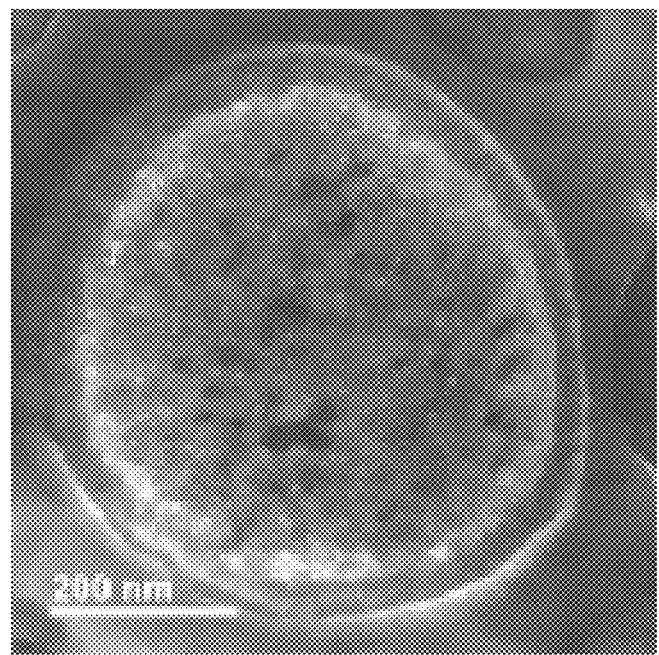
FIG. 4 illustrates a STEM image of Ag nanoparticles inside a MRSA SA62 drug resistant bacteria.

FIG. 4 illustrates a STEM image of silver (Ag) nanoparticles inside a MRSA SA62 drug resistant bacterium. The STEM image in coordination with Electron Diffraction Spectroscopy provided confirmation of disruption at sites of disulfide bonds and ferredoxins.

The use of nonionic silver nanoparticles made using laser ablation provides advantages over conventional silver nanoparticles, which are known to primarily function via release of silver ions and which have been shown to lead to antimicrobial silver nanoparticle resistance. As discussed above, conventional silver nanoparticles made using chemical reduction processes are known to lead to antimicrobial resistance, meaning their effective in killing microbes diminishes over time. Some studies have shown microbial resistance to ionic silver in as few as 6 generations.

In contrast, the spherical-shaped nanoparticles that can be included in the polymer compositions disclosed herein have been shown to have stable anti-microbial activity even after 28 passages/generations, with no diminution of antimicrobial activity, including no significant reduction in the MIC (minimum inhibitory concentration).

IV. UV Protective Function of Nanoparticles

Metal nanomaterials of the type disclosed herein and having diameters or sizes in the range of about 10 nm to 40 nm have loose dielectric fields. When a large quantity of particles are together, the dielectric effect on light waves passing through does not attenuate but can be frequency-shifted either to the red or to the blue end of the electromagnetic spectrum. Polymer compositions that have enough of such nanoparticles can affect the UV rays and shift them to the red end of the spectrum to reduce entry of photonic energy at a level that reduces overall damage.

In some embodiments, the polymer compositions can include metal nanoparticles having a high refractive index in order to reflect and/or scatter incident UV radiation. For example, nanoparticles used in the polymer compositions of the present disclosure can have a refractive index for UVA and/or UVB radiation of about 1.5 to about 4.6, or from about 2.0 to about 4.0, or from about 2.5 to about 3.5. In some embodiments, the refractive index of the nanoparticles will be higher with respect to UVB radiation relative to UVA radiation (e.g., the refractive index increases with decreasing wavelength). In other embodiments, however, the refractive index of the nanoparticles will be lower with respect to UVB radiation relative to UVA radiation (e.g., the refractive index increases with increasing wavelength).

In some embodiments, the polymer compositions can include nanoparticles having a photostability such that upon exposure to solar radiation (e.g., in an environment with a relatively high UV index of about 15), the nanoparticles do not degrade or lose effectiveness in protecting against UV radiation (e.g., remain about 100% as effective, or remain about 95-100% as effective, or about 90-100% as effective, or about 80-100% as effective) over at least a given time period (e.g., about 1 hour, or about 2-4 hours, or about 4-6 hours, about 6-12 hours or longer, or even indefinitely).

In some embodiments, a polymer composition exhibits radiation protection properties. For example, some embodiments include a plurality of nanoparticles (e.g., beryllium and/or gold) configured to absorb harmful radiation (e.g., alpha particles, beta particles, and/or gamma radiation), thereby reducing or eliminating an amount of radiation passing through the nanoparticle treated material.

In some embodiments, gold nanoparticles dispersed throughout a polymer composition down-convert incoming UV radiation into less harmful UV radiation. In some embodiments, the gold nanoparticles may down-shift incoming UV radiation by at least about 50 nm, or at least about 100 nm, or at least about 150 nm, such as by approximately 200 nm. In some embodiments, the gold nanoparticles may down-shift incoming UV radiation from UV light to visible light. In some embodiments, the gold nanoparticles may down-shift incoming UV radiation from UV wavelengths toward red and/or green wavelengths.

In some embodiments, gold nanoparticles dispersed throughout a polymer composition may absorb incoming UV radiation at a high energy and emit a lower energy wavelength, thereby imparting UV protection to the polymer composition and products made therefrom. Unexpectedly, the ability of the gold nanoparticles to perpetually perform this down-shift in wavelength/radiation energy does not appear to deteriorate with use. That is, the gold nanoparticles retained their UV protection capabilities and were not measurably degraded by incoming UV radiation. This beneficially prolongs the effectiveness of the polymer composition and products made therefrom. This also means that lower concentrations of gold nanoparticles or other wavelength-shifting metal nanoparticles may be used, resulting in products that are cheaper to produce while maintaining their integrity.

V. Fiber Spinning Polymer Compositions with Nanoparticles a. Electrospinning

The process of electrospinning is particularly suited for manufacturing polymer micro- and nanofibers. These fibers can then be applied to or incorporated into a variety of devices and surfaces. Many medical devices may be created using electro-spun fibers.

Figure 8A:
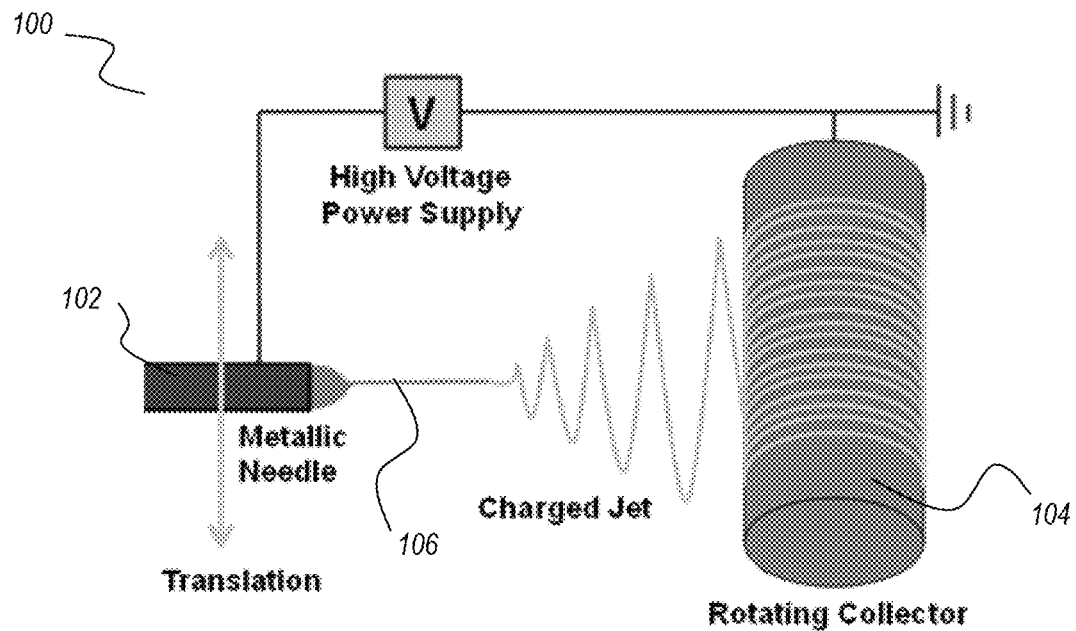
FIGS. 8A-8B illustrate schematic diagrams of example electrospinning and wet spinning processes, respectively.

FIG. 8A is a schematic diagram of an example electrospinning system 100. Electro-spun fibers are manufactured by applying a sufficiently high voltage to between a tip 102 and a collector 104. A polymer solution/melt 106 is contained within the tip 102. Application of a voltage charges the polymer solution/melt 106. Electrostatic repulsion counteracts surface tension to stretch the droplet. At a critical point, a charged liquid jet is formed passing toward the collector 104.

This charged liquid jet may be elongated by a whipping process caused by electrostatic repulsion initiated at small bends in the fiber. The fiber is ultimately deposited on and collected by the collector 104. The illustrated system 100 includes a rotating collector 104. Other embodiments may additionally or alternatively include other types of collectors, such as flat surface collectors.

The elongation and thinning of the fiber resulting from bending instability leads to the formation of uniform fibers with down to nanometer-scale diameters. Various solution parameters such as viscosity, polymer concentration, molecular weight, conductivity and/or surface tension play a role in the size and shape of the resulting fiber. Additional parameters may include voltage, tip-to-collector distance, feed rate, humidity, temperature, motion and size of the collector, and/or gauge of the tip 102.

By mixing metal nanoparticles with the polymer solution/melt 106, the resulting fibers incorporate the metal nanoparticles throughout the bulk and on the surface of the fibers.

b. Wet (Hydro) Spinning

Another manufacturing process for plastics, polymers and fibers is wet spinning (also referred to as hydrospinning). Similar to electrospinning, the process of wet spinning is particularly suited for manufacturing polymer micro- and nanofibers. These fibers can then be applied to or incorporated into a variety of devices and surfaces.

Figure 8B:
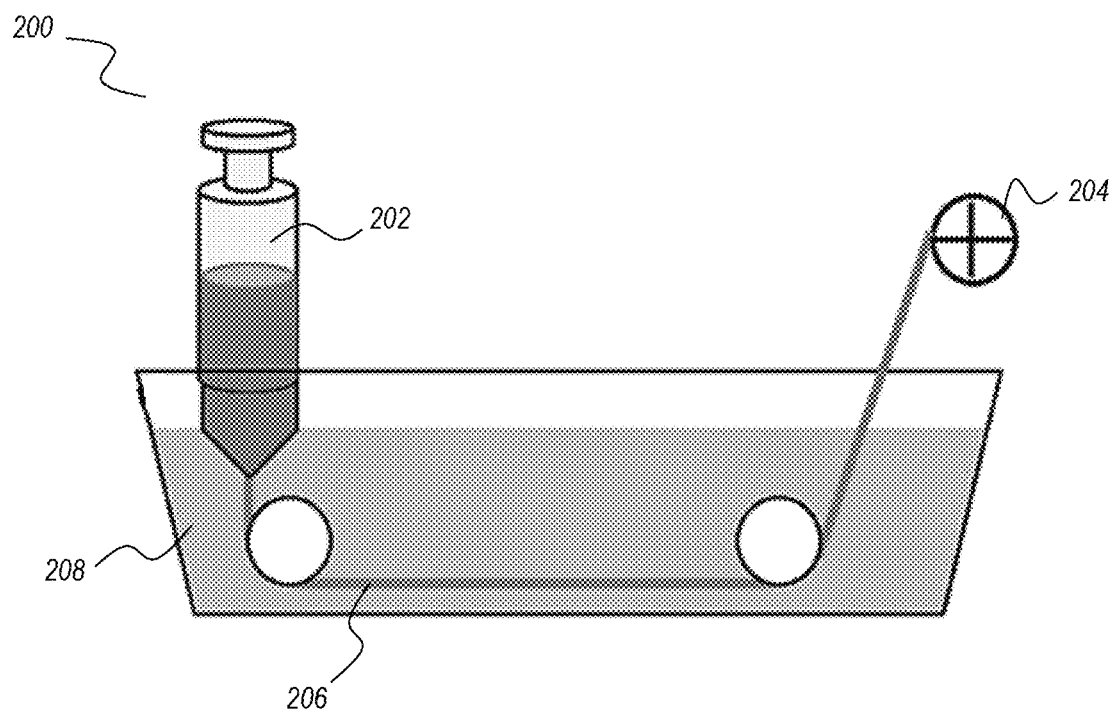

FIG. 8B is a schematic of an example wet spinning system 200. Wet spun fibers are created by injecting from a container 202 a polymer solution/melt 206 into a coagulation bath 208, which is typically water. As the polymer solution/melt 206 is injected or extruded into the bath 208, the injected stream will begin precipitating to form a fiber. This fiber can be spun or wound around a collector 204, such as a rotary collector. The polymer solution/melt 206 may be injected (or extruded) into the bath 208 using a spinneret or other appropriate instrument.

By mixing metal nanoparticles with the polymer solution/melt 206, the resulting fibers incorporate the metal nanoparticles throughout the bulk and on the surface of the fibers.

c. Example Polymer Solutions/Melts

Various polymers may be used as polymer solutions/melts in an electrospinning or wet spinning process, including any of the polymer compositions disclosed elsewhere herein of mixtures thereof. The selected polymer can depend on the desired characteristics of the resulting fiber and the ultimate application of the fiber. Industrial polymers, biodegradable polymers, specialty polymers and natural polymers are all suitable starting materials. Polymer matrix nanofiber composites can be produced using electrospinning with electrospinnable polymers. The polymer solutions/melts may include, or use as starting materials, resins and/or epoxies.

One or more fillers may be mixed with the polymer solution/melt prior to the fiber spinning process. Fillers may include but are not limited to: metal oxide nanoparticles (e.g., in addition to the metal nanoparticles disclosed herein), therapeutic agents, or combinations thereof. The therapeutic agents may include, but are not limited to, non-steroidal anti-inflammatory drugs (NSAIDs) and other anti-inflammatory drugs, antibiotics, pulmonary medications, anti-allergy drugs, antihistamines, vasodilators, muscle relaxers, steroids, anti-fungal agents, bronchial dilaters, nitroglycerin, cough suppressants, and/or other suitable therapeutic agents. The therapeutic agent incorporated into the polymer solution/melt will depend on the ultimate application of the resulting fibers (e.g., disposition on an implantable medical device) and/or the particular condition to be treated (e.g., allergies, bacterial infection, etcetera).

VI. Medical Devices

Polymer compositions manufactured using one or more of the methods disclosed herein can include medical devices. Medical devices formed in this manner are beneficially protected from UV radiation and microbial growth. Metal nanoparticles incorporated into the medical device are capable of down-converting incoming UV radiation to lower energy radiation. This beneficially prevents general degradation of the polymer-based device or article from UV radiation. The polymer-based devices or articles will be able to be used for longer periods of time without cracking, discoloration, fogging, leakage, and/or failing completely.

The metal nanoparticles incorporated into the medical device are also capable of deactivating or killing microbes, preventing microbial build up on or inside the medical devices. For example, the antimicrobial activity of the embedded nanoparticles can function to inhibit microbial growth and the production of biofilms on an implanted medical device. This beneficially prolongs the use of the devices in environments such as hospitals or clinics. This also benefits sterilization of the products, leading to lower costs in storage and sterilization procedures.

Examples of medical devices that may be formed, at least in part, using the methods disclosed herein include, but are not limited to, gloves, catheters, wound dressings, syringes and other drug delivery components, and polymeric portions of implantable devices (e.g., polymeric portions of pacemakers, replacement joints, drug pumps, intrauterine devices (IUDs), cochlear implants, vascular access devices, artificial heart valves), bone implants, bone pins, bone screws, tissue grafts, airway devices such as endotracheal tubes, catheters, arterio-venous grafts, by-pass grafts, anastomotic clips, arterial closure devices, patent foramen ovale closure devices, and drug delivery balloons.

The nanoparticle-impregnated fibers may be disposed on or form any portion of the structures of such devices. The nanoparticle-impregnated fibers may be disposed on an outer surface of such devices. Additionally, or alternatively, the nanoparticle-impregnated fibers may be disposed on an outer surface that contacts tissue or a tissue air interface (when the device is implanted).

Figure 9:
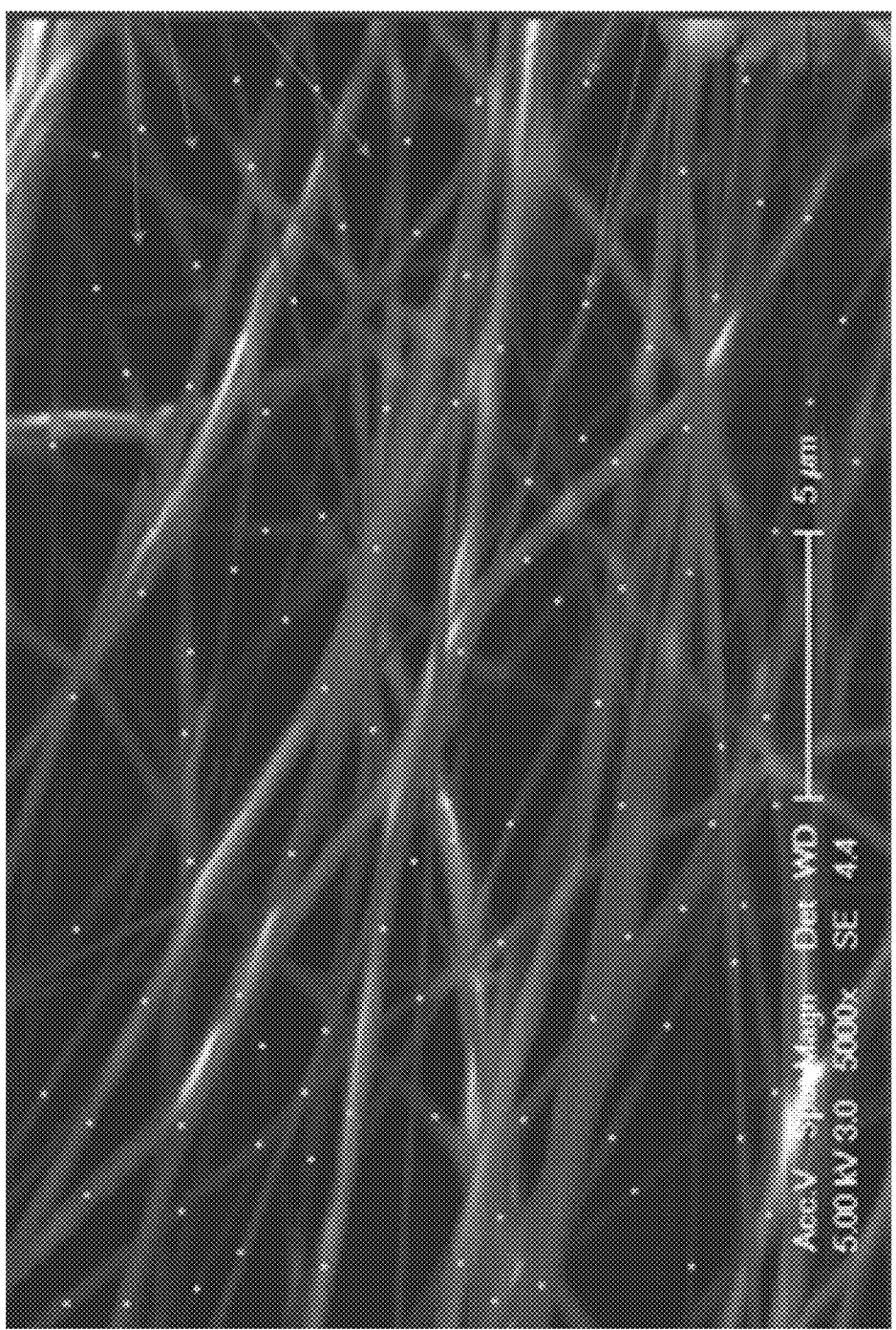
FIG. 9 is a rendering of nanoparticles embedded in an electrospun fiber.

FIG. 9 is a rendering of nanoparticles embedded in an electro-spun material. The embedded nanoparticles may be any of the nanoparticles discussed above, such as laser-ablated spherical nanoparticles, laser-ablated coral-shaped nanoparticles, metal oxide nanoparticles and/or combinations thereof.

VII. EXAMPLES

Example 1

Silver nanoparticles were suspended in 99.9% isopropyl alcohol. Inductive Coupled Plasma Optical Emission Spectrophotometry (ICPOES) was used to verify nanoparticle concentration. DLS was used to verify nanoparticle size, which was found to be approximately 6 to 10 nm. STEM imaging with Electron Loss Spectroscopy (ELS) verified surface composition and short bond lengths.

Drug resistant bacteria were found to be killed in concentration ranges of 0.5 mg/L (0.5 ppm) to 2 mg/L (2 ppm) of nanoparticles. The highest concentration found to kill drug resistant bacteria was 8 mg/L (8 ppm). STEM imaging using no stain and a dark field camera with 3 nm of carbon coating allowed for tracking of the nanoparticles within and around a bacterium. The STEM imaging in conjunction with Electron Diffraction Spectroscopy (EDS) provided confirmation of disruption at sites of disulfide bonds and ferredoxins.

Example 2

Figure 5A:
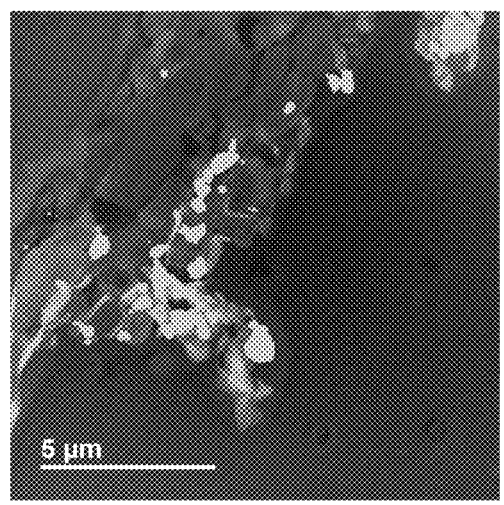
FIGS. 5A-5C illustrate STEM images of Tecoflex EG-93A-B20 thermoplastic impregnated with nanoparticles.
Figure 5B:
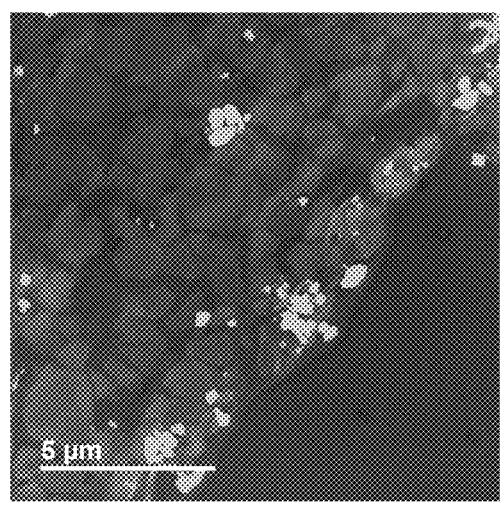
Figure 5C:
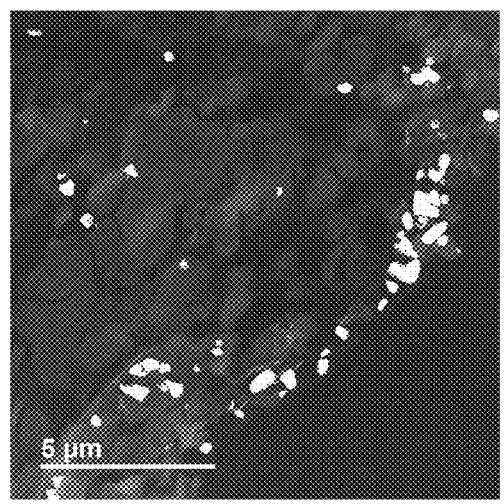
Figure 6A:
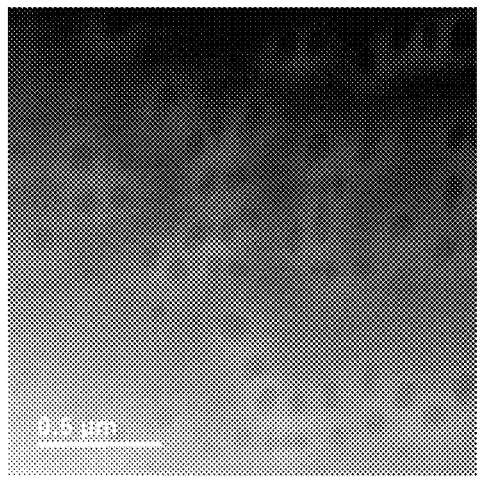
FIGS. 6A-6C illustrate STEM images of Isoplast 2510 thermoplastic impregnated with nanoparticles.
Figure 6B:
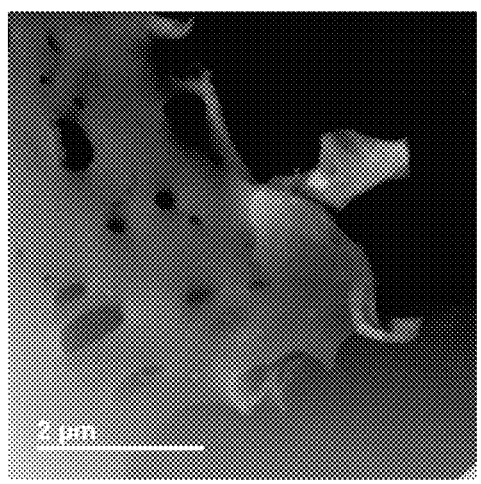
Figure 6C:
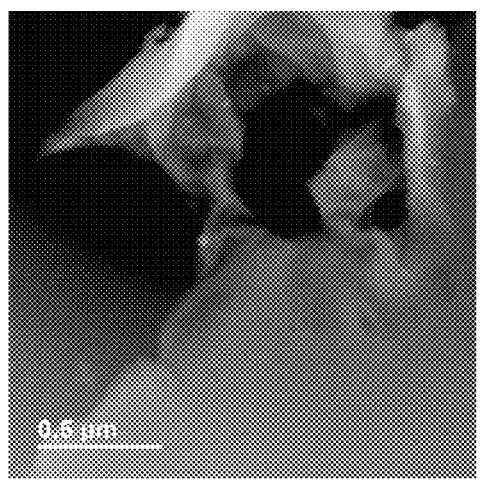
Figure 7A:
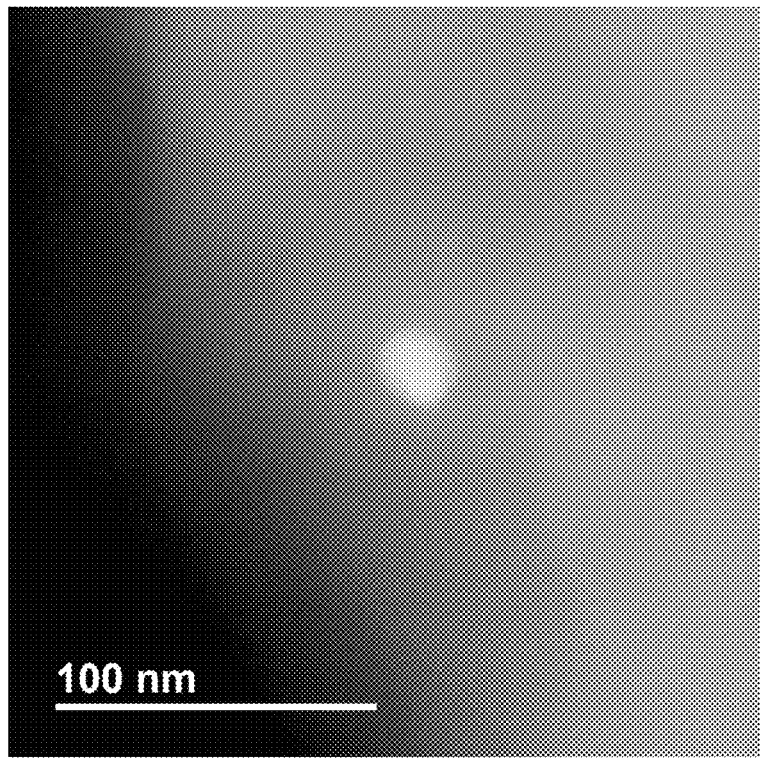
FIGS. 7A-7B illustrate a close-up STEM image of an embedded Ag nanoparticle in a thermoplastic.
Figure 7B:
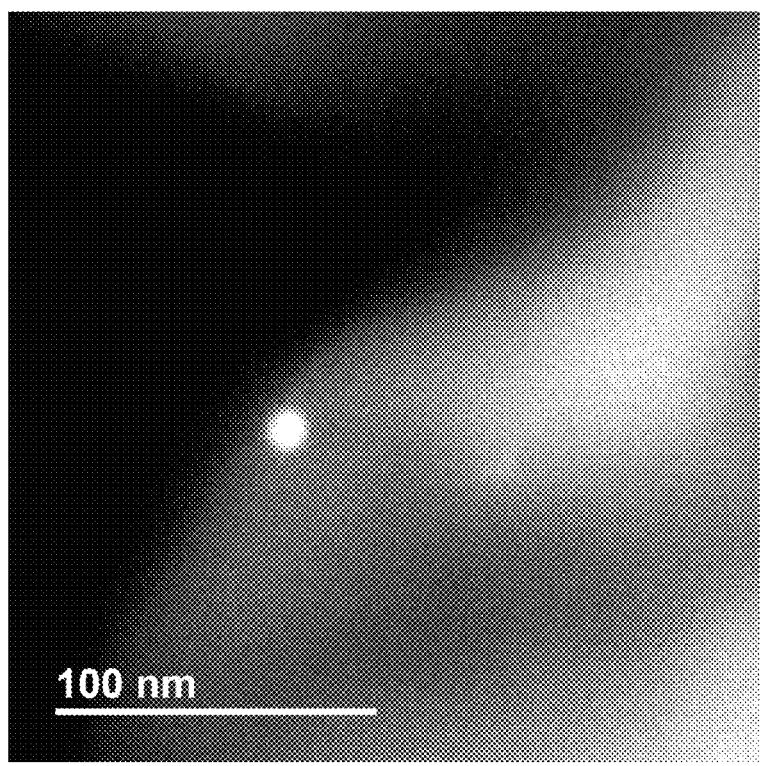

Polyethylene (PE) products embedded with silver nanoparticles were tested for antibacterial properties. Two polymers, Tecoflex FG-93A-B20 (W filament) and Isoplast 2510 (D filament), were provided and each were treated with silver nanoparticles. FIGS. 5A-C illustrate STEM images of Tecoflex EG-93A-B20 thermoplastic with embedded nanoparticles. FIGS. 6A-6C illustrate STEM images of Isoplast 2510 thermoplastic with embedded nanoparticles. FIGS. 7A-7B illustrate a silver nanoparticle embedded in a thermoplastic.

The silver nanoparticles were manufactured in isopropyl alcohol at a concentration of 38 mg/L (38 ppm). The alcohol mixture was applied to polymer beads or granules. The polymer beads or granules were melted for a final concentration of 6 mg/kg (6 ppm) in the resulting PE polymer. This concentration of 6 mg/kg had previously been successful in surface antibacterial testing. Extruded filaments were then embedded in toming polymer and tomed to an 80-100 nm thickness and mounted on 200 mesh formvar Carbon B TEM grids for imaging.

Imaging was performed on a JEOL 2800 Scanning Transmission Electron Microscope (STEM) with a darkfield camera, brightfield camera and a secondary surface camera. Element mapping to 1 nm$^2$ resolution was performed to identify nanoparticles and particulates, using a dual EDS detector for triangulation and net count accuracy.

The Tecoflex FG-93A-B20 thermoplastic was light purple in color and required a clenching or cooling stage after melt extrusion at 230° C. As shown in FIGS. 5A-C, under STEM, large solid metal particles hundreds of nanometers in size were observed. EDS mapping confirmed these to be barium sulfate.

Silver nanoparticles directly interact with sulfur chemistry and the overwhelming amount of barium sulfate (which is used as a filler and stiffener in Tecoflex FG-93A-B20) appears to have sequestered the silver nanoparticles. No direct nanoparticles were found on any grid from STEM imaging. Background silver was detected in the barium sulfate particles. Thermal disassociation was seen on the surface of the filaments, which was expected due to lack of thermal control in the final filament formation.

The Isoplast 2510 thermoplastic was darker purple in color and more glass like in surface finish. The Isoplast 2510 thermoplastic was melted at 230° C. and cooled at room temperature (22.5° C.). This thermoplastic used a phosphate as a filler and stiffener instead of barium sulfate. As shown in FIGS. 6A-6C, the phosphates did not interact with the Ag nanoparticles, and it was easy to find and element map the silver nanoparticles present. Isoplast 2510 is a more suitable candidate to create an equal distribution of the silver nanoparticles within the plastic. The surface did not have the same type of thermal disassociation.

Example 3

Surface antibacterial testing was conducted using the standard peni-cylinder method. The conventional peni-cylinder has an outside diameter of 7.8 mm, an inside diameter of 5.8 mm, and is 9.9 mm in length. The surface area can be calculated as:

$$A_s = \text{(Outside surface area)} + \text{(inside surface area)} + 2\text{(end surface area)}$$

$$A_s = 242.6 \text{ mm}^2 + 180.4 \text{ mm}^2 + 42 \text{ mm}^2$$

$$A_s = 465 \text{ mm}^2$$

Because the ends of the peni-cylinder have a 45° taper, the overall surface area is a little less than calculated but the difference is inconsequential.

20 mm long filament analogs to the peni-cylinder were used for antibacterial testing. The filament diameter was 1.2 mm and for every 1 mm in length there is 7.5 mm$^2$ of outside surface area and an ends surface area of 2.3 mm$^2$. A 20 mm long filament has a total surface area of $A_f = 152.3$ mm$^2$. The total number of filaments at 20 mm long needed to represent a peni-cylinder are:

$$A_s/A_f = 465/152.3 = 3.1$$

Three filaments were used in each testing sample set to approximately equal the surface area of one peni-cylinder surface. Metal nanoparticles were suspended throughout each filament.

The filaments were cleaved with a straight edge disposable razor cleaned with 70% or higher isopropyl alcohol. The filaments were measured against a serial surface that has two marks 20 mm apart and the filaments were cleaved to that length. The cut filaments were transferred to a 50 mL sample tube containing 25 mL of isopropyl alcohol and vortexed for 1 minute. The filaments were then removed, using tweezers that had been flame/heat sterilized, to a 50 mL sample holding container.

The antibacterial testing was performed using $E.\ coli$ at levels of 105, 106 and 107 colony forming units (CFU). Each set of three filaments were introduced to the $E.\ coli$ in tryptic soy broth for 1 hour of $E.\ coli$ exposure. Two sample sets (of three filaments) were used for each concentration of $E.\ coli$.

The filaments were removed from the tryptic soy broth containing the $E.\ coli$ colonies and allowed to drip until the filaments were free of fluids. The filaments were then introduced to dey-engley (DE) broth with a purple color. If any $E.\ coli$ bacteria grew from the filaments transferred to the DE broth, the color of the broth would turn yellow.

Samples of the DE broth were cultured for any colony growth on tryptic soy agar plates and compared with the cultures of the originally prepared 105, 106 and 107 CFUs. Colony counts were then made after 24 and 48 hours of growth. CFUs of the $E.\ coli$ were verified by agar counts: 105=23 CFUs; 106=256 CFUs; and 107=1000 CFUs.

After 24 hours of testing there were 0 CFUs on any of the filament agar plates for all prepared concentrations of $E.\ coli$. After 48 hours of testing there were 0 CFUs on any of the filament agar plates for all prepared concentrations of $E.\ coli$. The DE broth showed no color change for all prepared concentrations of $E.\ coli$ exposed to the filaments after 24 and 48 hours. There were no live bacteria on the surface of any of the filaments that were exposed for 1 hour to $E.\ coli$ concentrations of the 105, 106 and 107 CFUs. Duplicates of the testing showed the same results.

Example 4

Spherical-shaped silver nanoparticles made by laser ablation, with no external bond angles or edges, which are nonionic, and which do not release silver ions were tested to determine if they caused silver nanoparticle resistant bacteria. No such resistance was detected after 28 passages.

Two different types of spherical silver nanoparticles were tested: Silver Lot #Desktop Laser: Ag200917-104 (19 ppm) and Silver Lot #Industrial Laser: 171229-101 (16.8 ppm). The spherical-shaped silver nanoparticles made using the desktop laser had a mean diameter between 8-10 nm, and the spherical-shaped silver nanoparticles made using the industrial laser had a mean diameter between 8-12 nm.

The procedure for the study is outlined as follows:
Bacteria Preparation:
1. Streak bacteria onto tryptic soy agar (TSA) plates and incubate overnight 37° C.
2. Next day, inoculate 10 mL of silver with Mueller Hinton broth mix with one colony.
    a. Desktop laser:
        i. $E.\ coli$—Make a 4.75 ppm silver nanoparticle mix in the broth (2.5 mL Ag+7.5 mL broth).
        ii. $P.\ aeruginosa$—Make a 4.75 ppm silver nanoparticle mix in the broth (2.5 mL Ag+7.5 mL broth).
    b. Industrial laser:
        i. $E.\ coli$—Make a 2 ppm silver nanoparticle mix in the broth (1.2 mL Ag+8.8 mL broth).
        ii. $P.\ aeruginosa$—Make a 2 ppm silver nanoparticle mix in the broth (1.2 mL Ag+8.8 mL broth).
3. Incubate at 37° Cat 250 RPM 24-36 hours.
4. Monitor growth the next day.
5. Continue to serial passage in a new silver broth mixture with an inoculating loop into culture.
6. Every 5-7 days, streak out a loop of culture onto TSA plates to preserve passages then perform an MIC test on colonies to measure if the bacteria have generated resistance to the spherical silver nanoparticles.

The results of the study are as follows:
MIC Values:
$E.\ coli$—Industrial laser sample: MIC held at 2 ppm out to serial passage 28. DT laser sample: Culture stopped regenerating after passage 21. MIC held in previous passages.
$P.\ aeruginosa$—Industrial laser sample: MIC held at 2 ppm out to serial passage 28.
DT laser sample: Culture stopped regenerating after passage 21. MIC held in previous passages.
All negative and positive controls passed.

VIII. Additional Terms & Definitions

While certain embodiments of the present disclosure have been described in detail, with reference to specific configurations, parameters, components, elements, etcetera, the descriptions are illustrative and are not to be construed as limiting the scope of the claimed invention.

Furthermore, it should be understood that for any given element of component of a described embodiment, any of the possible alternatives listed for that element or component may generally be used individually or in combination with one another, unless implicitly or explicitly stated otherwise.

In addition, numbers expressing quantities, constituents, distances, or other measurements used in the specification and claims are to be understood as optionally being modified by the term "about." When the terms "about," "approximately," "substantially," or the like are used in conjunction with a stated amount, value, or condition, it may be taken to mean an amount, value or condition that deviates by less than 20%, less than 10%, less than 5%, less than 1%, less than 0.1%, or less than 0.01% of the stated amount, value, or condition. Optionally, numbers may be modified by the express use of the term "exactly" to clarify specific instances where the term "about" does not apply.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "medical device") may also include two or more such referents.

The embodiments disclosed herein should be understood as comprising/including disclosed components, and may therefore include additional components not specifically described. Optionally, the embodiments disclosed herein are essentially free or completely free of components that are not specifically described. That is, non-disclosed components may optionally be completely omitted or essentially omitted from the disclosed embodiments. For example, non-disclosed nanoparticle conjugates or non-disclosed solvents may optionally be completely omitted or essentially omitted from the polymer compositions and/or finished medical products disclosed herein.

An embodiment that "essentially omits" or is "essentially free of" a component may include trace amounts and/or non-functional amounts of the component. For example, an "essentially omitted" component may be included in an amount no more than 2.5%, no more than 1%, no more than 0.1%, or no more than 0.01% by total weight of the composition. This is likewise applicable to other negative modifier phrases such as, but not limited to, "essentially omits," "essentially without," similar phrases using "substantially" or other synonyms of "essentially," and the like.

A composition that "completely omits" or is "completely free of" a component does not include a detectable amount of the component (i.e., does not include an amount above any inherent background signal associated with the testing instrument) when analyzed using standard coating composition analysis techniques such as, for example, chromatographic techniques (e.g., thin-layer chromatography (TLC), gas chromatography (GC), liquid chromatography (LC)), or spectroscopy techniques (e.g., Fourier transform infrared (FTIR) spectroscopy).

It will also be appreciated that embodiments described herein may also include properties and/or features (e.g., ingredients, components, members, elements, parts, and/or portions) described in one or more separate embodiments and are not necessarily limited strictly to the features expressly described for that particular embodiment. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

The invention claimed is:

1. A method of manufacturing a polymer fiber using a fiber spinning process, the method comprising:
    providing metal nanoparticles formed via laser ablation, wherein the metal nanoparticles comprise spherical-shaped metal nanoparticles that are nonionic, have a mean diameter of 1 nm to 40 nm, and have a particle size distribution wherein at least 99% of the spherical-shaped metal nanoparticles have a particle size within 30% of the mean diameter and/or wherein at least 99% of the spherical-shaped metal nanoparticles have a diameter within ±3 nm of the mean diameter;
    mixing the metal nanoparticles with a polymer solution or polymer melt;
    drawing the polymer solution or polymer melt into a polymer fiber, the polymer solution or polymer melt thereby forming a polymer fiber in which the metal nanoparticles are incorporated; and
    collecting the polymer fiber on a collector.

2. The method of claim 1, wherein drawing the polymer solution or polymer melt into a fiber comprises an electrospinning process.

3. The method of claim 1, wherein drawing the polymer solution or polymer melt into a fiber comprises a wet spinning process.

4. The method of claim 1, wherein the metal nanoparticles comprise silver nanoparticles.

5. The method of claim 1, wherein the metal nanoparticles comprise gold nanoparticles.

6. The method of claim 1, wherein the polymer fiber comprises at least one polymer selected from the group consisting of silicone, epoxies, polystyrene (PS), polyethylene (PE), ethylene-vinyl acetate copolymer (EVA), polycarbonate (PC), polyurethane (PU), polyether ether ketone (PEEK), polylactic acid (PLA), polyhydroxyalkanoate (PHA), polyester (PES), polypropylene (PP), polyethylene terephthalate (PET), polymethyl methacrylate (PMMA), polybutylene terephthalate (PBT), phenol-formaldehyde (PF), nylon/polyimide (PA), melamine formaldehyde (MF), polytetrafluoroethylene (PTFE), polyvinyl chloride (PVC), polyvinyl pyrrolidone (PVP), acrylonitrile butadiene styrene (ABS), styrene block copolymer (SBC), rubber latex, nitriles, and combination thereof.

7. The method of claim 1, wherein the spherical-shaped metal nanoparticles have a particle size distribution wherein at least 99% of the spherical-shaped metal nanoparticles have a particle size within 20% of the mean diameter and/or wherein at least 99% of the spherical-shaped metal nanoparticles have a diameter within ±2 nm of the mean diameter.

8. The method of claim 1, wherein the spherical-shaped metal nanoparticles have a ξ-potential of at least about ±10 mV (absolute value).

9. The method of claim 1, wherein the metal nanoparticles further comprise coral-shaped nanoparticles.

10. The method of claim 1, wherein the polymer solution or polymer melt, after mixing, includes the metal nanoparticles at a concentration of about 50 ppb to about 100 ppm.

11. The method of claim 1, further comprising manufacturing a medical device, the medical device including the polymer fiber.

12. A polymer fiber formed by a process comprising:
    providing metal nanoparticles formed via laser ablation, wherein the metal nanoparticles comprise spherical-shaped metal nanoparticles that are nonionic, have a mean diameter of 1 nm to 40 nm, and have a particle size distribution wherein at least 99% of the spherical-shaped metal nanoparticles have a particle size within 30% of the mean diameter and/or wherein at least 99% of the spherical-shaped metal nanoparticles have a diameter within ±3 nm of the mean diameter;
    mixing the metal nanoparticles with a polymer solution or polymer melt;
    drawing the polymer solution or polymer melt into a polymer fiber, the polymer solution or polymer melt thereby forming a polymer fiber in which the metal nanoparticles are incorporated; and
    collecting the polymer fiber on a collector,
    wherein the polymer fiber comprises at least one organic polymer selected from the group consisting of epoxies, polystyrene (PS), polyethylene (PE), ethylene-vinyl acetate copolymer (EVA), polycarbonate (PC), polyurethane (PU), polyether ether ketone (PEEK), polylactic acid (PLA), polyhydroxyalkanoate (PHA), polyester (PES), polypropylene (PP), polyethylene terephthalate (PET), polymethyl methacrylate (PMMA), polybutylene terephthalate (PBT), phenol-formaldehyde (PF), nylon/polyimide (PA), melamine formaldehyde (MF) polytetrafluoroethylene (PTFE), polyvinyl chloride (PVC), polyvinyl pyrrolidone (PVP), acrylonitrile butadiene styrene (ABS), styrene block copolymer (SBC), rubber latex, nitriles, and combination thereof,
    wherein the polymer fiber includes the metal nanoparticles at a concentration of about 50 ppb to about 100 ppm.

13. The polymer fiber of claim 12, wherein the polymer fiber includes the metal nanoparticles at 0.5 mg/kg to about 8 mg/kg.

14. A method of manufacturing a polymer fiber using a fiber spinning process, the method comprising:
   providing metal nanoparticles formed via laser ablation, wherein the metal nanoparticles comprise spherical-shaped silver nanoparticles that are nonionic, have a mean diameter of 1 nm to 40 nm, and have a particle size distribution wherein at least 99% of the spherical-shaped silver nanoparticles have a particle size within 30% of the mean diameter and/or wherein at least 99% of the spherical-shaped silver nanoparticles have a diameter within ±3 nm of the mean diameter;
   mixing the metal nanoparticles with a polymer solution or polymer melt, wherein the polymer solution or polymer melt, after mixing, includes the metal nanoparticles at a concentration of about 50 ppb to about 100 ppm;
   drawing the polymer solution or polymer melt into a polymer fiber, the polymer solution or polymer melt thereby forming a polymer fiber in which the metal nanoparticles are incorporated; and
   collecting the polymer fiber on a collector.

15. The method of claim 14, wherein drawing the polymer solution or polymer melt into a fiber comprises an electro-spinning process.

16. The method of claim 14, wherein drawing the polymer solution or polymer melt into a fiber comprises a wet spinning process.

17. A polymer fiber formed by the method of claim 14, wherein the polymer fiber comprises at least one organic polymer selected from the group consisting of epoxies, polystyrene (PS), polyethylene (PE), ethylene-vinyl acetate copolymer (EVA), polycarbonate (PC), polyurethane (PU), polyether ether ketone (PEEK), polylactic acid (PLA), polyhydroxyalkanoate (PHA), polyester (PES), polypropylene (PP), polyethylene terephthalate (PET), polymethyl methacrylate (PMMA), polybutylene terephthalate (PBT), phenol-formaldehyde (PF), nylon/polyimide (PA), melamine formaldehyde (MF), polytetrafluoroethylene (PTFE), polyvinyl chloride (PVC), polyvinyl pyrrolidone (PVP), acrylonitrile butadiene styrene (ABS), styrene block copolymer (SBC), rubber latex, nitriles, and combination thereof,
   wherein the polymer fiber includes the metal nanoparticles at a concentration of about 50 ppb to about 100 ppm.

18. The polymer fiber of claim 17, wherein the polymer fiber includes the spherical-shaped silver nanoparticles at 0.5 mg/kg to about 8 mg/kg.

19. The polymer fiber of claim 12, wherein the spherical-shaped metal nanoparticles have a particle size distribution wherein at least 99% of the spherical-shaped metal nanoparticles have a particle size within 20% of the mean diameter and/or wherein at least 99% of the spherical-shaped metal nanoparticles have a diameter within ±2 nm of the mean diameter.

20. The method of claim 14, wherein the polymer fiber includes the metal nanoparticles at a concentration of about 100 ppb to about 50 ppm.

* * * * *